US010752564B2

(12) United States Patent
Schoonebeek et al.

(10) Patent No.: US 10,752,564 B2
(45) Date of Patent: *Aug. 25, 2020

(54) OXIDATIVE DEHYDROGENATION (ODH) OF ETHANE

(71) Applicant: SHELL OIL COMPANY, Houston, TX (US)

(72) Inventors: Ronald Jan Schoonebeek, Amsterdam (NL); Guss Van Rossum, Amsterdam (NL); Alouisius Nicolaas Renée Bos, Amsterdam (NL)

(73) Assignee: Shell Oil Company, Houston, TX (US)

(\*) Notice: Subject to any disclaimer, the term of this patent is extended or adjusted under 35 U.S.C. 154(b) by 0 days.

This patent is subject to a terminal disclaimer.

(21) Appl. No.: 16/319,933

(22) PCT Filed: Jul. 24, 2017

(86) PCT No.: PCT/EP2017/068614
§ 371 (c)(1),
(2) Date: Jan. 23, 2019

(87) PCT Pub. No.: WO2018/019760
PCT Pub. Date: Feb. 1, 2018

(65) Prior Publication Data
US 2019/0248716 A1    Aug. 15, 2019

(30) Foreign Application Priority Data
Jul. 26, 2016   (EP) ..................... 16181294

(51) Int. Cl.
*C07C 5/48* (2006.01)
*B01J 8/06* (2006.01)

(52) U.S. Cl.
CPC ............... *C07C 5/48* (2013.01); *B01J 8/067* (2013.01); *B01J 2208/00017* (2013.01); *B01J 2208/0053* (2013.01); *B01J 2208/00221* (2013.01); *B01J 2208/00513* (2013.01); *B01J 2208/065* (2013.01); *C07C 2523/28* (2013.01)

(58) Field of Classification Search
CPC ....... C07C 5/48; C07C 2523/28; C07C 11/04; B01J 8/067; B01J 2208/0053;
(Continued)

(56) References Cited

U.S. PATENT DOCUMENTS 6,977,064 B1 \* 12/2005 Adris ................. B01J 8/065
422/145
7,091,377 B2   8/2006 Borgmeier et al.
(Continued)

FOREIGN PATENT DOCUMENTS

EP    2716622 A1 \*  4/2014
EP    2716622 A1    4/2014
(Continued)

OTHER PUBLICATIONS

International Search Report and Written Opinion received for PCT Patent Application No. PCT/EP2017/068614, dated Oct. 16, 2017, 10 pages.
(Continued)

Primary Examiner — In Suk C Bullock
Assistant Examiner — Ali Z Fadhel

(57) ABSTRACT

Processes and associated reaction systems for the oxidative dehydrogenation of ethane are provided. In particular, a process is provided that comprises supplying a feed gas comprising ethane and oxygen to a multitubular fixed-bed reactor, allowing the ethane and oxygen to react in the presence of an oxidative dehydrogenation catalyst to yield a reactor effluent comprising ethylene; supplying a coolant to an upstream region of an interior shell space of the reactor in a flow pattern that is counter-current with the flow of the feed gas; and withdrawing the coolant from the upstream region and supplying at least a portion of the coolant withdrawn from the upstream region to the downstream region in a flow pattern that is co-current with the flow of the feed gas.

8 Claims, 1 Drawing Sheet

(58) Field of Classification Search
CPC .... B01J 2208/00221; B01J 2208/00513; B01J 2208/065; B01J 2208/00017; B01J 2523/56; B01J 2523/55; B01J 2523/64; B01J 2523/68; B01J 23/002
See application file for complete search history.

(56) References Cited

U.S. PATENT DOCUMENTS

| | | |
|---|---|---|
| 2004/0147393 A1 | 7/2004 | Hibst et al. |
| 2010/0256432 A1 | 10/2010 | Arnold et al. |
| 2015/0141727 A1* | 5/2015 | Simanzhenkov ......... C07C 5/48 585/658 |

FOREIGN PATENT DOCUMENTS

| | | |
|---|---|---|
| WO | 0185333 A2 | 11/2001 |
| WO | 03064035 A1 | 8/2003 |
| WO | 2010096909 A1 | 9/2010 |

OTHER PUBLICATIONS

International Search Report and Written Opinion received for PCT Patent Application No. PCT/EP2017/068615, dated Oct. 16, 2017, 10 pages.

Lopez et al., "Parametric Sensitivity of a Fixed Bed Catalytic Reactor: Cooling Fluid Flow Influence", Chemical Engineering Science, vol. 36, Issue No. 2, 1981, pp. 285-291.

\* cited by examiner

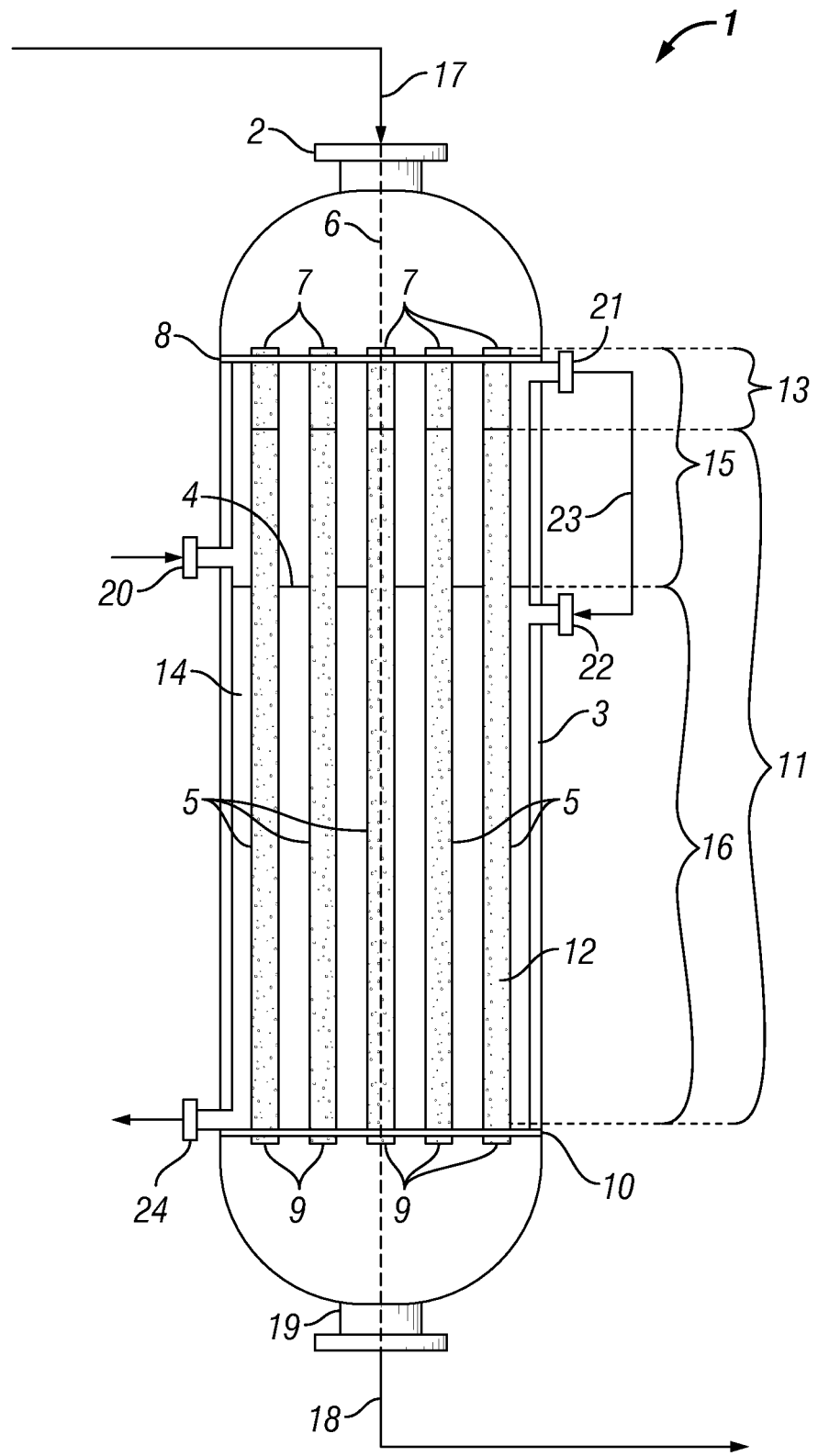

OXIDATIVE DEHYDROGENATION (ODH) OF ETHANE

CROSS REFERENCE TO RELATED APPLICATIONS

This is a national stage application of International Application No. PCT/EP2017/068614, filed 24 Jul. 2017, which claims benefit of priority to European Patent Application No. 16181294.6, filed 26 Jul. 2016.

FIELD OF THE INVENTION

The present invention relates to a process for the oxidative dehydrogenation of ethane.

BACKGROUND

It is known to oxidatively dehydrogenate ethane resulting in ethylene, in an oxidative dehydrogenation (oxydehydrogenation; ODH) process. Examples of ethane ODH processes are for example disclosed in U.S. Pat. No. 7,091,377, WO2003064035, US20040147393, WO2010096909 and US20100256432. The oxidative dehydrogenation of ethane converts ethane into ethylene. In this process, ethane is reacted with oxygen in the presence of an ODH catalyst to produce a product stream comprising predominately ethylene, along with unreacted reactants (such as ethane and oxygen), and typically other gases and/or by-products (such as carbon monoxide, carbon dioxide, water).

In general, the yield of ethylene in an ODH process is reduced by the undesirable combustion reactions of ethane and ethylene, both of which are highly exothermic and generate carbon dioxide and/or carbon monoxide. As is generally the case in such exothermic processes, it is important to control the reaction temperature within a certain range to maintain effective and safe plant operation and also to extend the life of the catalyst and inhibit undesirable side reactions. It is known that a multitubular fixed-bed reactor may be used to conduct such exothermic reactions, with the reactor employing a plurality of tubes containing a fixed bed of catalyst particulates, and a shell in which the tubes are contained through which coolant circulates to facilitate the removal of the reaction heat.

Typically, it is desirable to maintain isothermal conditions on the coolant side of the reactor. This is usually accomplished either by using a boiling medium (e.g. water/steam, kerosene) as the coolant, wherein the low-temperature incoming feed gas is preheated to the reaction temperature at the expense of the coolant which enters the shell at a higher temperature, or by circulating a coolant that is in counter-current flow with the flow of the reactants through the tubes at a sufficiently high circulation rate so as to rapidly remove heat. However, fixed bed reactors used in exothermic reactions may nevertheless have the propensity to develop one or more "hot spots" in various regions of the reactor.

In an attempt to avoid the undesirable formation of a so-called "hot-spot" (a localized temperature peak) in the catalyst bed, one commonly proposed solution is to reduce the diameter of the tubes in order to increase the heat transfer rate per unit volume of the catalyst. However, this typically increases the cost associated with building the reactor and also increases the amount of time required to load and unload the catalyst into the tubes. Similarly, it may also limit somewhat the size/shape of catalyst that can be used. Likewise, if the lengths of the tubes are significantly increased, the pressure drop across the reactor may also undesirably increase. Another commonly proposed solution is to operate at a lower productivity or lower conversion, for example by diluting the catalyst with an inert substance. However, this also has the disadvantage of increased cost and typically increases the difficulty of later recovering the spent catalyst from the reactor for regeneration, if desired.

Accordingly, the present inventors have sought to provide improved processes for the oxidative dehydrogenation of ethane. In particular, the present inventors have sought to provide ODH processes that utilize a multitubular fixed-bed reactor wherein the generation of hot-spots in the catalyst bed is avoided or reduced, thereby preventing or minimizing the risk of a reactor runaway.

SUMMARY

In one aspect, a process for the oxidative dehydrogenation of ethane to ethylene is provided, the process comprising:
providing a multitubular fixed-bed reactor comprising a reactor inlet, an interior shell space, a perforated partition that divides the interior shell space into an upstream region and a downstream region, and a plurality of reactor tubes, wherein the plurality of reactor tubes comprise a catalyst bed that comprises an oxidative dehydrogenation catalyst;
supplying a feed gas comprising ethane and oxygen to the reactor inlet and allowing the ethane and oxygen to react in the presence of the oxidative dehydrogenation catalyst to yield a reactor effluent comprising ethylene;
supplying a coolant to the upstream region in a flow pattern that is counter-current with the flow of the feed gas through the plurality of reactor tubes; and
withdrawing the coolant from the upstream region and supplying at least a portion of the coolant withdrawn from the upstream region to the downstream region in a flow pattern that is co-current with the flow of the feed gas through the plurality of reactor tubes.

BRIEF DESCRIPTION OF THE DRAWINGS

Some specific example embodiments of the disclosure may be understood by referring, in part, to the following description and the accompanying drawing.

FIG. 1 is a schematic illustration showing an exemplary embodiment of the present disclosure.

While the present disclosure is susceptible to various modifications and alternative forms, specific example embodiments have been shown in the FIGURE and are herein described in more detail. It should be understood, however, that the description of specific example embodiments is not intended to limit the invention to the particular forms disclosed, but on the contrary, this disclosure is to cover all modifications and equivalents as illustrated, in part, by the appended claims.

DETAILED DESCRIPTION

The present invention makes use of the observation that in an ODH process utilizing a multitubular fixed-bed reactor, hot-spots nearly always occur in an upstream portion of the catalyst bed; hence a low coolant temperature would be best here. However, at such a lower coolant temperature, there is quite some room for an axial temperature increase along the length of the reactor without the risk of a hot-spot forming in the downstream portion of the catalyst bed.

Accordingly, the present inventors have found that by utilizing the processes disclosed herein, it is possible to minimize or avoid the formation of hot-spots in an upstream portion of the catalyst bed, while simultaneously achieving relatively high productivity throughout the entire catalyst bed, without the need to decrease tube diameter and/or increase tube length of the tubes. In particular, it has been found that these advantages may be achieved by dividing the interior shell space of a multitubular fixed-bed reactor into an upstream region and a downstream region, and supplying coolant to the upstream and downstream regions in a flow pattern where, contrary to normal practice, the isothermicity of the coolant side is deliberately impaired by circulating coolant in the upstream region in counter-current flow with respect to the flow of the feed gas, and circulating coolant in the downstream region in co-current flow with respect to the flow of the feed gas at what would normally be considered an insufficient flow rate.

In accordance with the processes of the present disclosure, coolant is supplied to an upstream region of an interior shell space of a multitubular fixed-bed reactor in counter-current flow with respect to the flow of the feed gas through the plurality of reactor tubes. The temperature of the coolant in the upstream region will generally increase, due to removal of the reaction heat generated in the upstream portion of the catalyst bed, such that the coolant will be hotter when withdrawn from the upstream region at an upstream coolant outlet than when supplied to the upstream region at an upstream coolant inlet.

Coolant withdrawn from the upstream region is then supplied to a downstream region of the interior shell space of the multitubular fixed-bed reactor in co-current flow at a downstream coolant inlet that is fluidly connected to the upstream coolant outlet via a coolant circuit. As in the upstream region, the temperature of the coolant in the downstream region will also generally increase, due to the removal of the reaction heat generated in the downstream portion of the catalyst bed, such that the coolant will be hotter when withdrawn from the downstream region at a downstream coolant outlet than when supplied to the downstream region at a downstream coolant inlet.

In general, coolant is supplied to the upstream and downstream regions of the interior shell space of the reactor at a flow rate that is sufficiently low enough to allow for an increase in the temperature of the coolant during its flow through the respective upstream and downstream regions of the interior shell space of the reactor. For example, coolant may be supplied to the upstream region at a flow rate sufficient to allow for a coolant temperature increase of approximately 1 to 25° C., or 5 to 20° C., or from 5 to 15° C. in the upstream region, as measured from an upstream coolant inlet positioned at or near the bottom of the upstream region to an upstream coolant outlet positioned at or near the top of the upstream region.

Similarly, coolant may be supplied to the downstream region at a flow rate sufficient to allow for a coolant temperature increase of approximately 1 to 30° C., or 5 to 25° C., or from 5 to 20° C. in the downstream region, as measured from a downstream coolant inlet positioned at or near the top of the downstream region to a downstream coolant outlet positioned at or near the bottom of the downstream region. As such, the reactor is operated in a manner where the isothermicity of the coolant side is deliberately compromised by utilizing counter-current flow in the upstream region and co-current coolant flow in the downstream region, at what would generally be considered too low of a flow rate, which thereby conversely allows for the process side to become remarkably isothermal.

In accordance with the oxidative dehydrogenation processes of the present disclosure, a feed gas comprising ethane and oxygen is supplied to the inlet of a multitubular fixed-bed reactor. As used herein, the term "feed gas" is understood to refer to the totality of the gaseous stream(s) at the inlet(s) of the reactor. Thus, as will be appreciated by one skilled in the art, the feed gas is often comprised of a combination of one or more gaseous stream(s), such as an ethane stream, an oxygen-containing stream, a recycle gas stream, etc. Optionally, in addition to ethane and oxygen, the feed gas may further comprise other alkanes (e.g. methane, propane), carbon monoxide, carbon dioxide, hydrogen, steam, an inert gas (such as nitrogen, helium and/or argon), and/or various by-products of the ODH reaction (e.g. acetylene, acetic acid).

Ethane and oxygen may be added to the reactor as mixed feed, optionally comprising further components therein, at the same reactor inlet. Alternatively, the ethane and oxygen may be added in separate feeds, optionally comprising further components therein, to the reactor at the same reactor inlet or at separate reactor inlets. Further, the order and manner in which the components of the feed gas are supplied to the reactor inlet is not particularly limited, and therefore, the components may be combined simultaneously or sequentially. Further, the components of the feed gas may optionally be vaporized, preheated and mixed (if desired) prior to being supplied to the reactor inlet using means known to those skilled in the art. For example, preheat techniques may include, for example, heat exchange from steam, a heat transfer fluid (e.g. coolant), reactor effluent, and/or a furnace.

Ethane in the feed gas may be from any suitable source, including natural gas, provided that impurities are sufficiently removed therefrom and may include fresh ethane, a recycle of unreacted ethane from the reactor effluent, or a combination thereof. Similarly, the oxygen may originate from any suitable source, such as air or a high purity oxygen stream. Such high-purity oxygen may have a purity of greater than 90%, preferably greater than 95%, more preferably greater than 99%, and most preferably greater than 99.4%.

In general, the molar ratio of molecular oxygen to ethane in the feed gas at the reactor inlet may be in the range of from 0.01 to 1, more suitably 0.05 to 0.5. Preferably, the feed gas comprises from 5 to 35 vol. % of oxygen, relative to the total volume of the feed gas, more suitably 20 to 30 vol. % of oxygen, and 40 to 80 vol. % of ethane, more suitably 50 to 70 vol. % ethane, and less than 80 (0 to 80) vol. % of an inert gas, more suitably less than 50 (0 to 50) vol. % of an inert gas, more suitably 5 to 35 vol. % of an inert gas, most suitably 10 to 20 vol. % of an inert gas. Suitably, the oxygen concentration in the feed gas should be less than the concentration of oxygen that would form a flammable mixture at either the reactor inlet or the reactor outlet at the prevailing operating conditions.

Multitubular fixed-bed reactors suitable for use in the present disclosure are not particularly limited and may include any of a variety known in the art. In general, a suitable multitubular fixed-bed reactor comprises a reactor inlet, an interior shell space, a perforated partition that divides the interior shell space into an upstream region and a downstream region, and a plurality of reactor tubes, wherein the plurality of reactor tubes comprise a catalyst bed that comprises an oxidative dehydrogenation catalyst. Optionally, in addition to the catalyst bed, the reactor tubes may further comprise a bed of an inert material.

Within the reactor, the upper ends of the reactor tubes are typically fixed in place by an upper tube plate and are in fluid communication with the reactor inlet. Similarly, the lower ends of the reactor tubes are typically fixed in place by a lower tube plate and are in fluid communication with the reactor outlet. Preferably, the reactor tubes are arranged within the reactor in a substantially vertical manner such that they are no more than 5° from vertical, and the upper and lower tube plates are positioned within the reactor in a substantially horizontal manner such that they are no more than 3° from horizontal.

While the size and number of reactor tubes within a multitubular fixed-bed reactor may vary widely from reactor to reactor, a reactor tube used in a commercial reactor may generally have a length of from 1 to 25 meters and an internal tube diameter of from 10 to 80 millimeters. Further, the number of reactor tubes can vary and may range in the thousands, for example up to 50,000.

A perforated partition extending transverse to the plurality of reactor tubes divides the interior shell space of the reactor into an upstream region and a downstream region. In general, the perforated partition is a plate having a plurality of holes through which the reactor tubes can pass. A perforated partition may be of any suitable material, such as metal (e.g. carbon steel).

The perforated partition is typically arranged such that the upstream region is at least 10% of the reactor tube length, or at least 15%, or at least 20%, or at least 25%, on the same basis, and at most 70% of the reactor tube length, or at most 40%, or at most 30%, or at most 25%, or at most 20%, or at most 15%, on the same basis, or from 10% to 30% of the reactor tube length, or from 10% to 25%, or from 10% to 20%, or from 10% to 15%, or from 15% to 30%, or from 15% to 25%, or from 15% to 20%, on the same basis. Correspondingly, the downstream region is typically at least 30% of the reactor tube length, or at least 60%, or at least 70%, or at least 75%, or at least 80%, or at least 85%, on the same basis, and at most 90% of the reactor tube length, or at most 85%, or at most 80%, or at most 75%, one the same basis, or from 70% to 90%, or from 75% to 90%, or from 80% to 90%, or from 70% to 85%, or from 75% to 85%, or from 80% to 85%, one the same basis. Advantageously, by dividing the interior shell space into two separate regions, it is possible to improve the distribution of the coolant in the reactor, thereby providing more control over the temperature.

In accordance with the ODH processes of the present disclosure, ethane and oxygen are allowed to react in the presence of an oxidative dehydrogenation catalyst to yield a reactor effluent comprising ethylene. In general, various ODH processes are known and described in the art and the ODH processes of the present disclosure are not limited in that regard. Thus, the person skilled in the art may conveniently employ any of such processes in accordance with the ODH processes of the present disclosure. For example, suitable ODH processes, including catalysts and other process conditions, include those described in above-mentioned U.S. Pat. No. 7,091,377, WO2003064035, US20040147393, WO2010096909 and US20100256432, which are herein incorporated by reference.

Suitably, the temperature in the plurality of reactor tubes is in the range of from 100 to 600° C., preferably in the range of from 200 to 500° C. Further, the pressure in the plurality of reactor tubes is in the range of from 1 to 30 bara (i.e. "bar absolute"), or from 1 to 20 bara, or from 1 to 15 bara, or from 2 to 10 bara, or from 3 to 10 bara.

Oxidative dehydrogenation catalysts suitable for use in the present disclosure are not particularly limited and may include any ethane oxidative dehydrogenation catalyst. The amount of such catalyst is not essential. Preferably, a catalytically effective amount of the catalyst is used, that is to say an amount sufficient to promote the ethane oxydehydrogenation reaction.

Examples of suitable oxidative dehydrogenation catalyst include, but are not necessarily limited to, one or more mixed metal oxide catalyst comprising molybdenum, vanadium, niobium and optionally tellurium as the metals and may have the following formula:

$$Mo_1V_aTe_bNb_cO_n$$

wherein:

a, b, c and n represent the ratio of the molar amount of the element in question to the molar amount of molybdenum (Mo);

a (for V) is from 0.01 to 1, preferably 0.05 to 0.60, more preferably 0.10 to 0.40, more preferably 0.20 to 0.35, most preferably 0.25 to 0.30;

b (for Te) is 0 or from >0 to 1, preferably 0.01 to 0.40, more preferably 0.05 to 0.30, more preferably 0.05 to 0.20, most preferably 0.09 to 0.15;

c (for Nb) is from >0 to 1, preferably 0.01 to 0.40, more preferably 0.05 to 0.30, more preferably 0.10 to 0.25, most preferably 0.14 to 0.20; and n (for O) is a number which is determined by the valency and frequency of elements other than oxygen.

Optionally, a catalyst bed may comprise more than one oxidative dehydrogenation catalyst. For example, in one embodiment, a catalyst bed may comprise a plurality of oxidative dehydrogenation catalysts having varied activity levels (e.g. so as to vary the activity level along the length of the reactor tube). Further, if desired, the catalyst bed may further comprise inert material (e.g. to dilute and/or reduce the activity of the catalyst bed). Optionally, in another embodiment, a catalyst bed may comprise an oxidative dehydrogenation catalyst comprising tellurium in an upstream catalyst bed positioned within the upstream region and an oxidative dehydrogenation/oxygen removal catalyst in a downstream catalyst bed positioned within the downstream region.

Preferably, the oxidative dehydrogenation catalyst is heterogeneous and in the form of particles. Further, preferably, said heterogeneous catalyst is porous, specifically a porous, particulate catalyst.

As mentioned, in accordance with the processes of the present disclosure, coolant is supplied to an upstream region of the interior shell space of a multitubular fixed-bed reactor in a flow pattern that is counter-current with the flow of the feed gas through the plurality of reactor tubes. The coolant is typically supplied to the upstream region via an upstream coolant inlet located at or near the bottom of the upstream region. Similarly, coolant is typically removed from the upstream region via an upstream coolant outlet located at or near the top of the upstream region.

Coolant may be supplied to, and removed from, the upstream region of the interior shell space of the reactor in any suitable manner so long as the flow of the coolant in the upstream region is counter-current with the flow of the feed gas through the plurality of reactor tubes. Typically, coolant is supplied to the upstream region via a coolant circuit, which optionally comprises one or more cooling apparatus (e.g. heat exchanger, steam drum, etc.) and one or more circulation pumps.

Further, in accordance with the processes of the present disclosure, coolant is supplied to the downstream region of the interior shell space of the multitubular fixed-bed reactor in a flow pattern that is co-current with the flow of the feed gas through the plurality of reactor tubes. The coolant is supplied to the downstream region via a downstream coolant inlet that is fluidly connected to the upstream coolant outlet and is typically located at or near the top of the downstream region. Coolant is removed from the downstream region via a downstream coolant outlet located at or near the bottom of the downstream region. Coolant may be supplied to, and removed from, the downstream region of the interior shell space of the reactor in any suitable manner so long as the flow of the coolant in the downstream region is co-current with the flow of the feed gas through the plurality of reactor tubes. Typically, coolant is supplied from the upstream region to the downstream region via a coolant circuit, which optionally comprises a cooling apparatus (e.g. heat exchanger, steam drum, etc.) and a circulation pump.

Coolant is preferably supplied to the upstream region of the interior shell space of the reactor at a flow rate sufficient to allow for a coolant temperature increase of approximately 1 to 25° C., or 5 to 20° C., or from 5 to 15° C. as measured from an upstream coolant inlet positioned at or near the bottom of the upstream region to an upstream coolant outlet positioned at or near the top of the upstream region.

Similarly, coolant is preferably supplied to the downstream region at a flow rate sufficient to allow for a coolant temperature increase of approximately 1 to 30° C., or 5 to 25° C., or from 5 to 20° C., as measured from a downstream coolant inlet positioned at or near the top of the downstream region to a downstream coolant outlet positioned at or near the bottom of the downstream region.

As will be appreciated by one skilled in the art, suitable upstream and downstream coolant flow rates may vary widely depending, at least in part, on the specific configuration of the multitubular fixed-bed reactor (e.g. the length and internal diameter of the tubes within the reactor, the comparative size of the upstream and downstream regions), process conditions, the activity level of the ODH catalyst employed, the size and/or shape of the catalyst employed, as well as the particular heat capacity of the coolant. It is within the ability of one skilled in the art to select suitable upstream and downstream coolant flow rates, taking into consideration, for example, the above-mentioned parameters. Suitably, if desired, simulation models can be used to determine the appropriate coolant flow rates needed in order to achieve the desired coolant temperature differentials. Reference is made to, for example, A. Soria Lopez, et al., "Parametric Sensitivity of a Fixed Bed Catalytic Reactor", Chemical Engineering Science, Volume 36 (1981), pp. 285-291 for further discussion relating to the effects of temperature variation in a co-current coolant on the operation of a fixed bed reactor. Suitable coolant may be any fluid suitable for heat transfer, for example, a molten salt or an organic material suitable for heat exchange (e.g. oil, kerosene, etc.). Preferably, cooling in the present process is performed under non-boiling conditions. In particular, it is preferred that in the present process the coolant does not boil.

Suitably, the upstream inlet coolant temperature is typically at least 250° C., or at least 275° C., or at least 300° C., or at least 310° C., or at least 320° C., and typically at most 499° C., or at most 450° C., or at most 425° C., or at most 400° C., or at most 380° C., or from 250° C. to 499° C., or from 250° C. to 400° C., or from 300° C. to 400° C., or from 320° C. to 380° C.

Further, in accordance with the processes of the present disclosure, coolant is preferably supplied to the downstream region of the interior shell space of the reactor via the downstream coolant inlet at a downstream inlet coolant temperature (i.e. the temperature of the coolant as measured at the downstream coolant inlet) that exceeds that of the upstream inlet coolant temperature (i.e. the temperature of the coolant as measured at the upstream coolant inlet) by at least 1° C., or at least 3° C. greater, or at least 5° C. greater, or at least 10° C. greater, and typically at most 25° C. greater, or at most 20° C. greater, or at most 15° C., or from 1° C. to 25° C. greater, or from 5° C. to 25° C. greater, or from 5° C. to 20° C. greater, or from 5° C. to 15° C. greater.

Suitably, the downstream inlet coolant temperature is typically at least 251° C., or at least 255° C., or at least 260° C., or at least 275° C., or at least 285° C., or at least 300° C., or at least 310° C., or at least 320° C., and typically at most 500° C., or at most 450° C., or at most 425° C., or at most 400° C., or at most 380° C., or from 251° C. to 500° C., or from 255° C. to 500° C., or from 260° C. to 500° C., or from 251° C. to 400° C., or from 300° C. to 400° C., or from 320° C. to 380° C.

Optionally, the heat that is removed from the reactor may be used to heat the feed gas and/or the coolant that is supplied to the reactor. Further, if desired, the removed heat may also be used for steam generation (or boiler feed water preheat) for use as an energy source, including as steam itself or further transformed into power.

In a further embodiment of the present invention, the coolant withdrawn from the upstream region is split into at least two portions, and one of the at least two split coolant portions is supplied to the downstream region in a flow pattern that is co-current with the flow of the feed gas through the plurality of reactor tubes. In said embodiment, the relative amount of the split coolant portion that is supplied to the downstream region, on the basis of the total amount of coolant withdrawn from the upstream region, is suitably of from 30 to 70 vol. %, more suitably of from 40 to 60 vol. %, most suitably of from 45 to 55 vol. %.

Reference is now made to FIG. 1, which is a schematic view of a reaction system for the oxidative dehydrogenation of ethane, according to certain embodiments of the present disclosure. It will be clear to the skilled person, that as a schematic diagram this FIGURE does not show all necessary inputs, outputs, recycle streams, etc. that may be present in the reaction system. Furthermore, in the FIGURE, as will be appreciated, elements can be added, exchanged, and/or eliminated so as to provide any number of additional embodiments. In addition, as will be appreciated, the proportion and the relative scale of the elements provided in the FIGURE is intended to illustrate the embodiments of the present disclosure, and should not be taken in a limiting sense.

It should additionally be appreciated that the orientation/configuration shown in FIG. 1 is not intended to be limiting or exhaustive of all possible orientations/configurations, but rather it is intended to be merely an example provided to illustrate the spirit of the invention. For example, the inlet of the reactor is illustrated as being positioned at the top of the reactor with the flow of reactants proceeding downward towards the outlet of the reactor positioned at the bottom; however, it should be understood that the orientation may vary from that depicted in FIG. 1. For example, the reactor orientation may be inverted from that shown in FIG. 1 such that the inlet of the reactor is positioned, for example, at the bottom of the reactor with the flow of reactants proceeding upward towards an outlet positioned at the top of the reactor.

Multitubular fixed-bed reactor (1) comprises reactor inlet (2), reactor shell (3), perforated partition (4) and a plurality of open-ended reactor tubes (5) positioned substantially parallel to the central longitudinal axis (6) of reactor (1). The upper ends (7) of the reactor tubes (5) are connected to a substantially horizontal upper tube plate (8) and the lower ends (9) of the reactor tubes (5) are connected to a substantially horizontal lower tube plate (10). The upper tube plate (8) and the lower tube plate (10) are supported by the inner wall of reactor (1).

Reactor tubes (5) contain a catalyst bed (11) comprising an oxidative dehydrogenation catalyst (12). In addition to catalyst bed (11), reactor tubes (5) may optionally further comprise a bed of inert material, such as inert bed (13). Typically, catalyst bed (11) is supported in the reactor tubes (5) by a catalyst support means (not shown) arranged in the lower ends (9) of the reactor tubes (5).

Perforated partition (4) is a plate having a plurality of apertures through which reactor tubes (5) can pass. Perforated partition (4) divides interior shell space (14) into upstream region (15) and downstream region (16).

In accordance with the processes of the present disclosure, a feed gas (17) comprising ethane and oxygen is supplied to reactor (1) via one or more inlets, such as reactor inlet (2) which is in fluid communication with the upper ends (7) of the reactor tubes (5). In reactor tubes (5), feed gas (17) contacts catalyst bed (11). Contact of the feed gas in the presence of oxidative dehydrogenation catalyst (12) at appropriate reaction conditions, as described above, converts at least a portion of the ethane to ethylene, water and reaction byproducts, if any. Reactor effluent (18) exits the reactor (1) via one or more outlets, such as reactor outlet (19) which is in fluid communication with the lower ends (9) of the reactor tubes (5).

As shown in FIG. 1, coolant is supplied to upstream region (15) via upstream coolant inlet (20) and is removed from upstream region (15) via upstream coolant outlet (21). Further, coolant is supplied to downstream region (16) via downstream coolant inlet (22), which is fluidly connected to upstream coolant outlet (21) via coolant circuit (23), and is removed from downstream region (16) via downstream coolant outlet (24). In both the upstream and downstream regions, the circulating coolant will take up heat by contact with the reactor tubes (5) such that the coolant will generally be hotter when withdrawn from the upstream or downstream coolant outlet than when it is supplied to the respective upstream or downstream coolant inlet. Suitably, a cooling apparatus (not shown) may optionally be used to remove heat from the coolant before it is supplied to the upstream and/or downstream regions. Optionally, interior shell space (14) may be provided with baffles (not shown) to guide coolant.

As previously mentioned, coolant is supplied to upstream region (15) in a flow pattern that is counter-current with the flow of the feed gas through the reactor tubes (5) and is supplied to downstream region (16) in a flow pattern that is co-current with the flow of the feed gas through the reactor tubes (5). Coolant is preferably supplied to upstream region (15) at a flow rate such that the upstream outlet coolant temperature as measured at upstream coolant outlet (21) will exceed the upstream inlet coolant temperature as measured at upstream coolant inlet (20) by 1 to 25° C. Coolant is preferably supplied to downstream region (16) at a flow rate such that the downstream outlet coolant temperature as measured at downstream coolant outlet (24) will exceed the downstream inlet coolant temperature as measured at downstream coolant inlet (22) by 1 to 30° C.

The present invention is also applicable to a process for oxidative dehydrogenation of alkanes having a higher carbon number than ethane, in particular alkanes having a carbon number of from 3 to 6 carbon atoms, including propane, butane, pentane and hexane, more specifically propane and butane, most specifically propane.

The invention is further illustrated by the following Examples.

Examples

In the present Examples, a process for the oxidative dehydrogenation (ODH) of ethane to ethylene is carried out in a multitubular fixed-bed reactor comprising a reactor inlet, an interior shell space, a perforated partition that divides the interior shell space into an upstream region and a downstream region, except for (reference) Example 1 (wherein no such partition is used), and a plurality of reactor tubes, wherein the reactor tubes comprise a catalyst bed that comprises an oxidative dehydrogenation catalyst. The length of each tube is 6 metres. The inner diameter of each tube is 0.75 inch (1.91 cm).

A feed gas comprising ethane and oxygen is supplied to the reactor inlet. The temperature of the feed gas at said inlet is 160° C. The ethane and oxygen are allowed to react in the presence of the above-mentioned catalyst to yield a reactor effluent comprising ethylene. Further, a molten-salt coolant is supplied to the upstream region in a flow pattern that is counter-current with the flow of the feed gas through the reactor tubes, the coolant is withdrawn from the upstream region, and the coolant withdrawn from the upstream region is supplied to the downstream region in a flow pattern that is co-current with the flow of the feed gas through the reactor tubes. A set-up for performing Examples 2, 3 and 4 is shown in FIG. 1.

In the upstream part of the reactor, the temperature of the process stream comprising reactants and/or products (hereinafter referred to as "process temperature") increases as a consequence of the exothermic ethane ODH reaction taking place. Said process temperature equals the catalyst temperature. Moving along the reactor length starting from the upstream reactor inlet, said process temperature increases to a certain maximum (peak) temperature, after which the process temperature would decrease because the ethane concentration decreases resulting in less heat production. A relatively high peak temperature for the process stream, as compared to the average process stream temperature, is disadvantageous in that this increases the risk of a reactor runaway.

In the present Examples, the effect of the above-mentioned perforated partition, and its position along the reactor length, on the difference between peak process temperature and average process temperature is assessed. Generally, the greater the latter temperature difference the greater the likelihood of a reactor runaway is. The temperature data (in ° C.), and positions of the perforated partition (distance in metres) relative to the upstream top side, in relation to a variety of cases are shown in Table 1 below. For Examples 2, 3 and 4, respectively, the upstream region is 63%, 37% and 25%, respectively, of the length of the reactor tubes.

For Examples 2-4, the temperature data (in ° C.) in Table 1 also include: 1) the difference between the outlet coolant temperature and the inlet coolant temperature in the upstream region ($3^{rd}$ column of Table 1); 2) the difference between the outlet coolant temperature and the inlet coolant temperature in the downstream region ($4^{th}$ column of Table 1); and 3) the difference between the inlet coolant temperature in the downstream region and the inlet coolant temperature in the upstream region (5th column of Table 1).

In (reference) Example 1, no perforated partition is used (that is to say, no separate upstream and downstream regions), and the coolant is supplied to the entire interior shell space in a flow pattern that is counter-current with the flow of the feed gas through the reactor tubes wherein the coolant is supplied to an inlet at the bottom and withdrawn at an outlet at the top. In said Example 1, the difference between the outlet coolant temperature (355° C.) and the inlet coolant temperature (350° C.) is 5° C. In all of Examples 2-4, the difference between the downstream outlet coolant temperature (355° C.) and the upstream inlet coolant temperature (350° C.) is also 5° C.

Further, in the present Examples, the space-time-yield (STY) is set at 700 g of ethylene per liter of catalyst per hour. Further, the ethane conversion is set at 55% and the ethylene selectivity at 87%. Said STY and ethane conversion are kept constant at said levels by adjustment of catalyst activity. The total and partial pressures of ethane ($C_2H_6$) and oxygen ($O_2$) at the upstream reactor inlet are kept constant: $P_{total}$=6 bar; $pC_2H_6$=4.2 bar; $pO_2$=1.8 bar. The gas hourly space velocity (GHSV) is 1950 $hr^{-1}$. The coolant flow rate is kept constant at 1,000 kg/hour/tube.

TABLE 1

| | | Δ [$T_{Cou}$ − $T_{Ciu}$] | Δ [$T_{Cod}$ − $T_{Cid}$] | Δ [$T_{Cid}$ − $T_{Ciu}$] | Δ [$T_{Pp}$ − $T_{Pa}$] |
|---|---|---|---|---|---|
| Ex. 1 | none | n.a. | n.a. | n.a. | 17.9 |
| Ex. 2 | 3.8 m | 3 | 2 | 3 | 12.8 |
| Ex. 3 | 2.2 m | 2 | 3 | 2 | 9.1 |
| Ex. 4 | 1.5 m | 0 | 5 | 0 | 7.2 |

Ex. = Example;
n.a. = not applicable;
$T_{Cou}$ = upstream outlet coolant temperature;
$T_{Ciu}$ = upstream inlet coolant temperature;
$T_{Cod}$ = downstream outlet coolant temperature;
$T_{Cid}$ = downstream inlet coolant temperature;
$T_{Pp}$ = peak process temperature;
$T_{Pa}$ = average process temperature Surprisingly, it appears from the results in Table 1 above that by providing a perforated partition in the reactor (thereby creating an upstream region and a downstream region) and by having a counter-current coolant flow in the upstream region and a co-current coolant flow in the downstream region, the difference between peak process temperature and average process temperature can advantageously be kept relatively small, thereby preventing or minimizing the above-mentioned risk of a reactor runaway. The difference between peak process temperature and average process temperature is advantageously only 12.8° C. (Example 2), 9.1° C. (Example 3) and 7.2° C. (Example 4) as opposed to 17.9° C. in Example 1 (reference) wherein no perforated partition is used.

That which is claimed is:

1. A process for the oxidative dehydrogenation of ethane to ethylene comprising:
providing a multitubular fixed-bed reactor comprising a reactor inlet, an interior shell space, a perforated partition that divides the interior shell space into an upstream region and a downstream region, and a plurality of reactor tubes, wherein the plurality of reactor tubes comprise a catalyst bed that comprises an oxidative dehydrogenation catalyst;
supplying a feed gas comprising ethane and oxygen to the reactor inlet and allowing the ethane and oxygen to react in the presence of the oxidative dehydrogenation catalyst to yield a reactor effluent comprising ethylene;
supplying a coolant to the upstream region in a flow pattern that is counter-current with the flow of the feed gas through the plurality of reactor tubes; and
withdrawing the coolant from the upstream region and supplying at least a portion of the coolant withdrawn from the upstream region to the downstream region in a flow pattern that is co-current with the flow of the feed gas through the plurality of reactor tubes,
wherein the coolant is supplied to the downstream region at a downstream coolant inlet at a downstream inlet coolant temperature and is withdrawn from the downstream region at a downstream coolant outlet at a downstream outlet coolant temperature, and wherein the downstream outlet coolant temperature exceeds the downstream inlet coolant temperature by 1 to 30° C.

2. The process of claim 1, wherein the coolant is supplied to the upstream region at an upstream coolant inlet at an upstream inlet coolant temperature of from 250° C. to 499° C.

3. The process of claim 1, wherein the coolant is supplied to the upstream region at an upstream coolant inlet at an upstream inlet coolant temperature of from 250° C. to 400° C.

4. The process of claim 1, wherein the coolant is supplied to the downstream region at a downstream coolant inlet at a downstream inlet coolant temperature of from 251° C. to 500° C.

5. The process of claim 1, wherein the coolant is supplied to the upstream region at an upstream coolant inlet at an upstream inlet coolant temperature and is withdrawn from the upstream region at an upstream coolant outlet at an upstream outlet coolant temperature, and wherein the upstream outlet coolant temperature exceeds the upstream inlet coolant temperature by 1 to 25° C.

6. The process of claim 1, wherein the coolant is supplied to the upstream region at an upstream coolant inlet at an upstream inlet coolant temperature and is supplied to the downstream region at a downstream coolant inlet at a downstream inlet coolant temperature, and wherein the downstream inlet coolant temperature exceeds the upstream inlet coolant temperature by 1 to 25° C.

7. The process of claim 1, wherein the upstream region is from 10 to 30% of the length of the reactor tubes.

8. The process of claim 1, wherein the oxidative dehydrogenation catalyst in the catalyst bed has the following formula:

$Mo_1V_aTe_bNb_cO_n$ wherein:
a, b, c and n represent the ratio of the molar amount of the element in question to the molar amount of molybdenum;
a is from 0.01 to 1;
b is 0 or from >0 to 1;
c is from >0 to 1; and
n is a number which is determined by the valency and frequency of elements other than oxygen.

* * * * *

UNITED STATES PATENT AND TRADEMARK OFFICE
CERTIFICATE OF CORRECTION

PATENT NO. : 10,752,564 B2
APPLICATION NO. : 16/319933
DATED : August 25, 2020
INVENTOR(S) : Ronald Jan Schoonebeek, Guss Van Rossum and Alouisius Nicolaas Renee Boss It is certified that error appears in the above-identified patent and that said Letters Patent is hereby corrected as shown below:

On the Title Page

Item (72), should read:
Ronald Jan Schoonebeek, Amsterdam (NL);
Guus Van Rossum, Amsterdam (NL);
Alouisius Nicolaas Reene Bos, Amsterdam (NL)

Signed and Sealed this
First Day of June, 2021

Drew Hirshfeld
*Performing the Functions and Duties of the
Under Secretary of Commerce for Intellectual Property and
Director of the United States Patent and Trademark Office*